United States Patent
Gremillion

(10) Patent No.: US 11,452,850 B2
(45) Date of Patent: Sep. 27, 2022

(54) METHOD AND APPARATUS FOR DELIVERING A DRUG

(71) Applicant: Grayson Matthew Gremillion, New Orleans, LA (US)

(72) Inventor: Grayson Matthew Gremillion, New Orleans, LA (US)

(*) Notice: Subject to any disclaimer, the term of this patent is extended or adjusted under 35 U.S.C. 154(b) by 248 days.

(21) Appl. No.: 16/734,495

(22) Filed: Jan. 6, 2020

(65) Prior Publication Data

US 2020/0215315 A1 Jul. 9, 2020

Related U.S. Application Data

(62) Division of application No. 15/265,424, filed on Sep. 14, 2016, now Pat. No. 10,525,241.

(51) Int. Cl.
*A61M 31/00* (2006.01)
*A61M 5/31* (2006.01)

(52) U.S. Cl.
CPC .......... *A61M 31/002* (2013.01); *A61M 5/31* (2013.01); *A61M 2210/0618* (2013.01)

(58) Field of Classification Search
CPC .................. A61M 5/31; A61M 2210/0618
See application file for complete search history.

(56) References Cited

U.S. PATENT DOCUMENTS

| 4,994,028 A * | 2/1991 | Leonard ............ A61M 37/0069 604/59 |
| 6,063,079 A | 5/2000 | Hovda et al. |
| 8,025,635 B2 | 9/2011 | Eaton et al. |
| 8,795,713 B2 * | 8/2014 | Makower ................ A61L 15/42 424/435 |
| 2007/0073282 A1 | 3/2007 | McGaffigan et al. |
| 2013/0338700 A1 | 12/2013 | Matheny |
| 2015/0100133 A1* | 4/2015 | Xie .......................... A61F 2/186 623/23.7 |
| 2015/0133851 A1* | 5/2015 | Reif ..................... A61K 9/0043 604/22 |

FOREIGN PATENT DOCUMENTS

WO 2008008389 1/2008

* cited by examiner

*Primary Examiner* — Bradley J Osinski
(74) *Attorney, Agent, or Firm* — Baker Donelson

(57) ABSTRACT

In the specification and drawings a method and apparatus for delivering a drug into a nasal turbinate or nasal polyp is described and shown, which can include implanting a drug eluting implant into a nasal turbinate or nasal polyp; and leaving the drug eluting material in the nasal turbinate or nasal polyp for at least one day such that a drug is released from the drug eluting implant over a period of time.

10 Claims, 7 Drawing Sheets

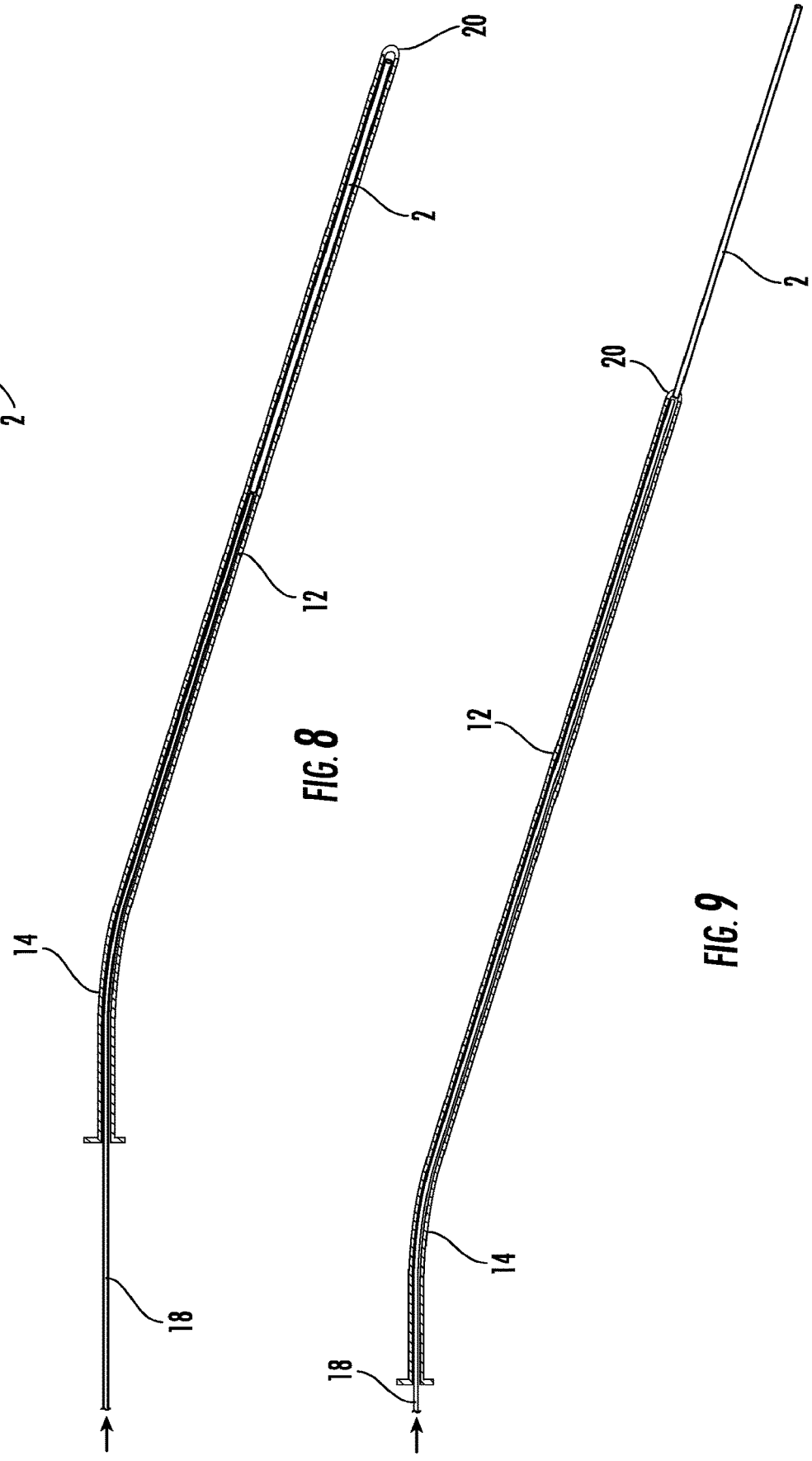

METHOD AND APPARATUS FOR DELIVERING A DRUG

I. CROSS-REFERENCE TO RELATED APPLICATION

Not Applicable.

II. STATEMENT REGARDING FEDERALLY SPONSORED RESEARCH OR DEVELOPMENT

Not Applicable.

III. THE NAMES OF THE PARTIES TO A JOINT RESEARCH AGREEMENT'

Not Applicable.

IV. INCORPORATION-BY-REFERENCE OF MATERIAL SUBMITTED ON A COMPACT DISC

Not Applicable.

V. BACKGROUND

Allergic rhinitis, nasal congestion and nasal polyposis are significant medical issues that affect millions of people around the world. The nasal turbinates are one of the major causes of nasal obstruction. The turbinates can become hypertrophied and produce increased amounts of mucous when irritated by environmental allergens, hormones in the body, or some medicines. Steroids can decrease the reactivity of the turbinates to allergens and hormones. Steroids can be delivered in multiple ways to the human body. For example, steroids can be injected into veins or muscles to decrease inflammation. A potential problem that can be associated with the injection of steroids into veins or muscles is that there can be side effects to the entire body when this is done. Another way that steroids can be delivered to the human body is via an aqueous solution containing steroid molecules that is sprayed, for example daily or twice daily, into the nose to help decrease inflammation and hypertrophy. There are also some aerosol preparations available. However, it can be difficult for a patient to comply with a daily or twice daily application schedule, and the application may not be done as prescribed. This can lead to treatment failures. There can also be a significant amount of nasal bleeding because the sprays can thin the mucosa on the septum.

The application of steroids to the inferior turbinate decreases the size of the turbinate therefore decreasing nasal obstruction and allowing the patient to breath better. In the past, physicians would sometimes inject aqueous solutions of steroid directly into the turbinates. In many cases this worked well for control of allergic rhinitis and shrunk the inferior turbinates considerably for months at a time. However, this practice has been all but abandoned because some patients developed blindness after injection within about twenty-four hours of injection, and usually within one hour of injection. It is hypothesized that the small size of the particle in an aqueous solution would travel within a vein in the turbinate back to the vein going to the eye and cause blindness.

Other ways of decreasing the size of the turbinate can include destruction of the native tissue either through "chewing" the tissue and causing scarring, or by ablation with radiofrequency or electrocautery. These are inherently destructive to the tissue and cause damage to the native tissue. They also do not fix the allergic component of the problem, only the hypertrophy and nasal congestion components.

Patients also can develop polyps in their nose, which can be caused by allergies to substances in the environment. These patients often need surgery to remove the polyps so that they can breathe through their nose. These polyps are actually overgrowths of mucosa which can block the nasal passage. The polyps are also susceptible to injection with aqueous steroid solutions and shrink up when injected. A potential problem with this approach is that the liquid preparations stay in the system for only a short time and the polyps increase in size again once the steroids are gone.

VI. BRIEF DESCRIPTION OF THE SEVERAL VIEWS OF THE DRAWINGS

FIG. 7 is a side elevation view of an embodiment described herein.

FIG. 8 is a side elevation view of an embodiment described herein, with the hollow bore needle shown as partially transparent.

FIG. 9 is a side elevation view of an embodiment described herein, with the hollow bore needle shown as partially transparent.

VII. DETAILED DESCRIPTION

Figure 1:
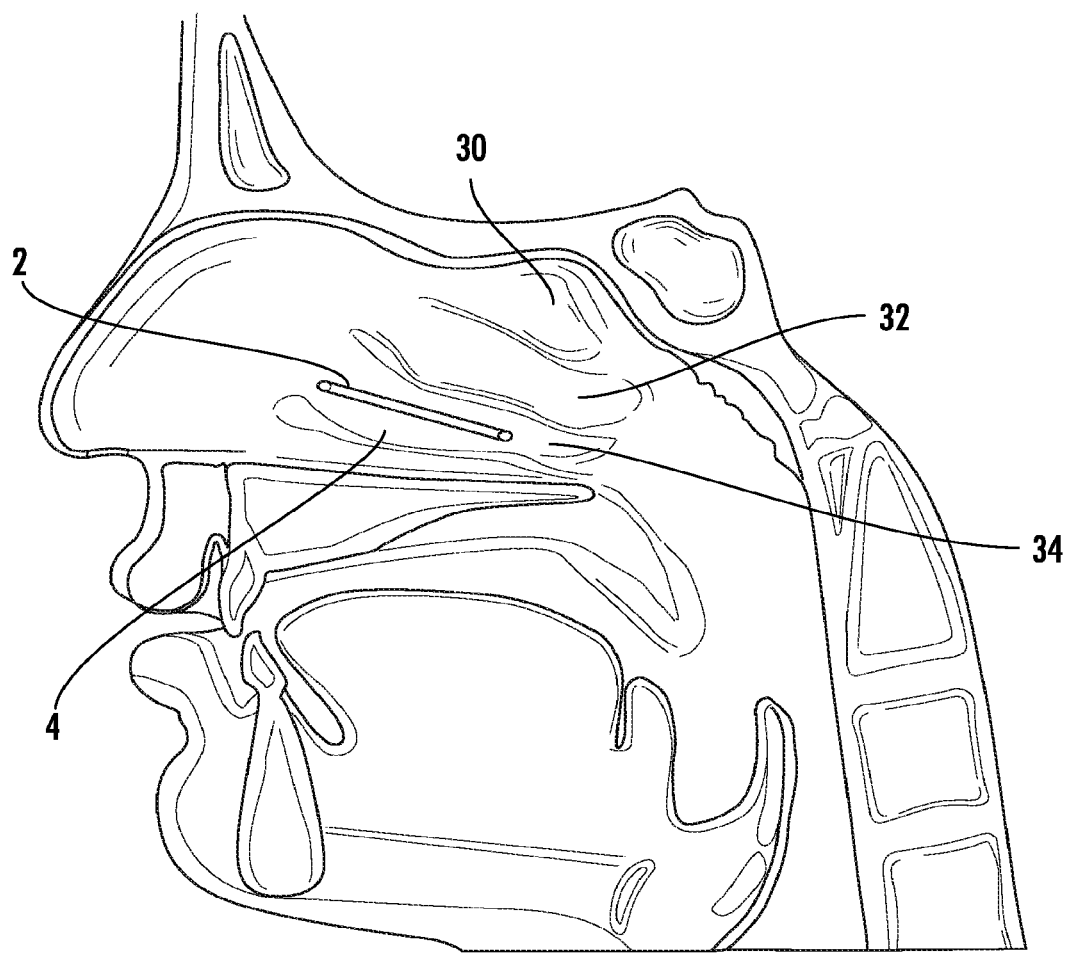
FIG. 1 is a cross sectional side view of the sinus region of a person and shows an embodiment described herein.

As required, detailed embodiments of the present invention are disclosed herein. However, it is to be understood that the disclosed embodiments are merely exemplary of the invention, which can be embodied in various forms. As such, any feature(s) used in one embodiment can be used in another embodiment. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

Alternate embodiments may be devised without departing from the spirit or the scope of the invention. Additionally, well-known elements of exemplary embodiments of the invention will not be described in detail or will be omitted so as not to obscure the relevant details of the invention.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The terms "connected" and/or "coupled," as used herein, are defined as connected, although not necessarily directly, and not necessarily mechanically.

Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

Herein various embodiments of the present invention are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Figure 10:
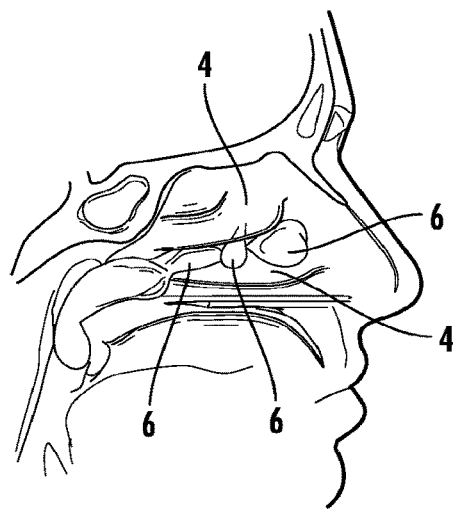
FIG. 10 is a cross sectional side view of the sinus region of a person and shows an embodiment described herein.
Figure 11:
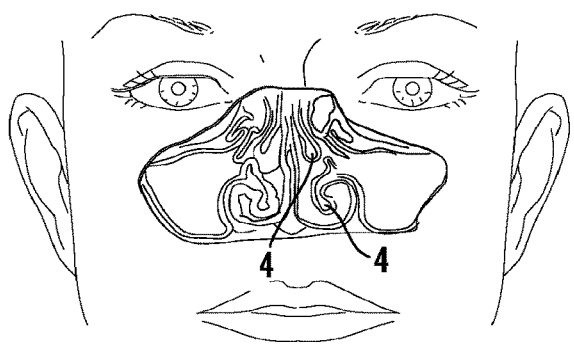
FIG. 11 is a cross sectional front view of the sinus region of a person and shows an embodiment described herein.

Described now are exemplary embodiments of the present invention. Referring now to the drawings, beginning with FIGS. 1 to 9, an exemplary embodiment of a method and apparatus for delivering a drug into nasal tissue, such as into the nasal turbinate or intranasal polyp, is shown and described. In an embodiment, a drug eluting material is implanted into a nasal turbinate or nasal polyp. The drug eluting material can be one or more implants 2 that are implanted into a nasal turbinate 4 and/or nasal polyp 6 (shown in FIGS. 10 to 12). In an embodiment, the drug can include one or more steroids, corticosteroids, antihistamines, and/or other drugs. The method and apparatus can be used to treat a number of conditions, including but not limited to turbinate hypertrophy (shown in the left half of FIG. 11), nasal congestion, allergic rhinitis, and nasal polyposis.

In an embodiment, the delivery apparatus can include a syringe 10, such as a 3-5 cc medical syringe. In an embodiment, the needle 12 is a 5 cc sterile Luer-Lok tip syringe, product number 309646.

The syringe 10 is attached to a needle 12, such as a hollow bore 10-27 gauge spinal needle. In an embodiment, the needle 12 has a length of between about 1.5 inches and 7 inches. In an embodiment the needle 12 is a Spinocan product number S22475 or S2735, with a gauge of between 18 and 27. The needle 12 can have a bend 14 which can allow for easier placement of a drug into the nasal tissue.

Figure 2:
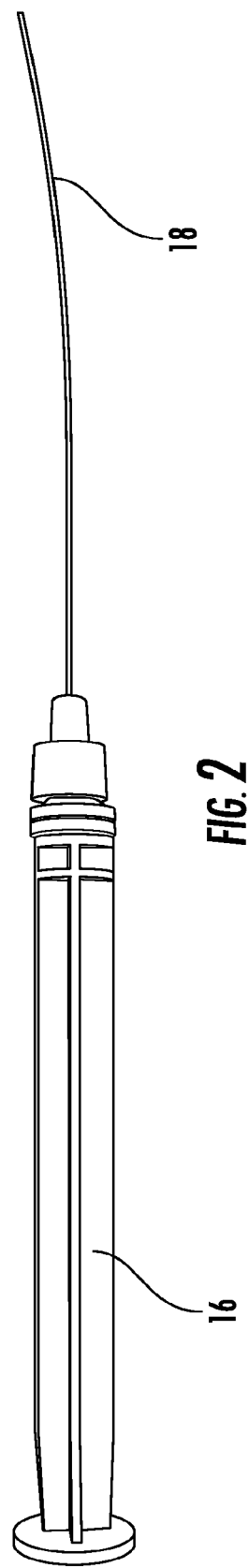
FIG. 2 is a side elevation view of an embodiment described herein.
Figure 3:
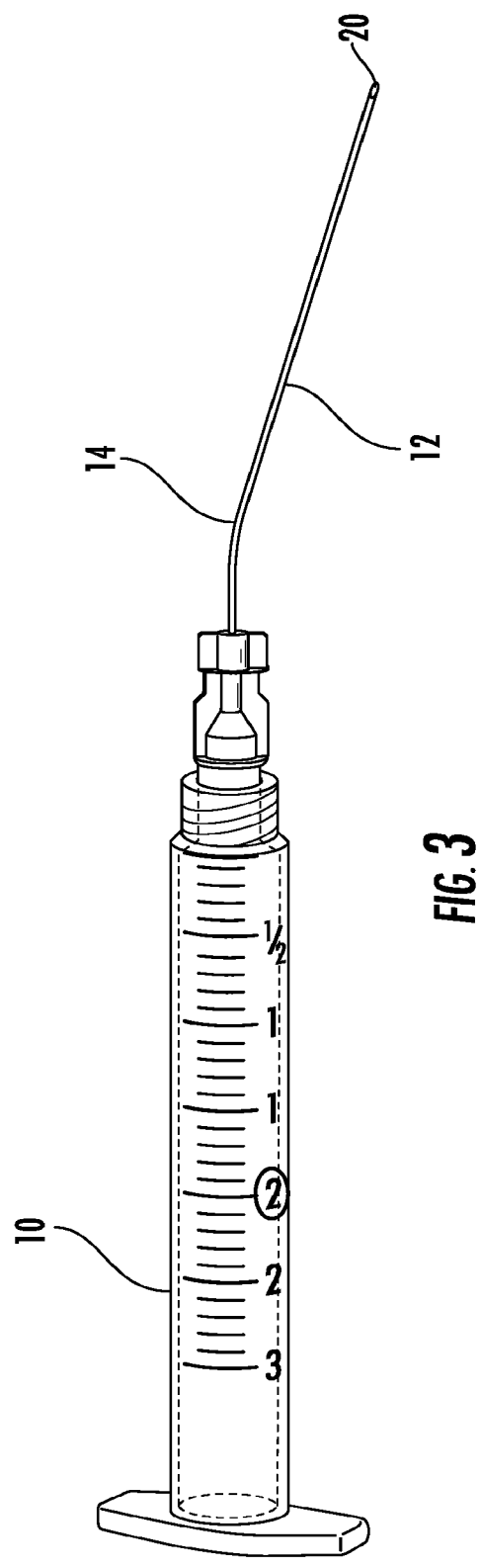
FIG. 3 is a side elevation view of an embodiment described herein.
Figure 4:
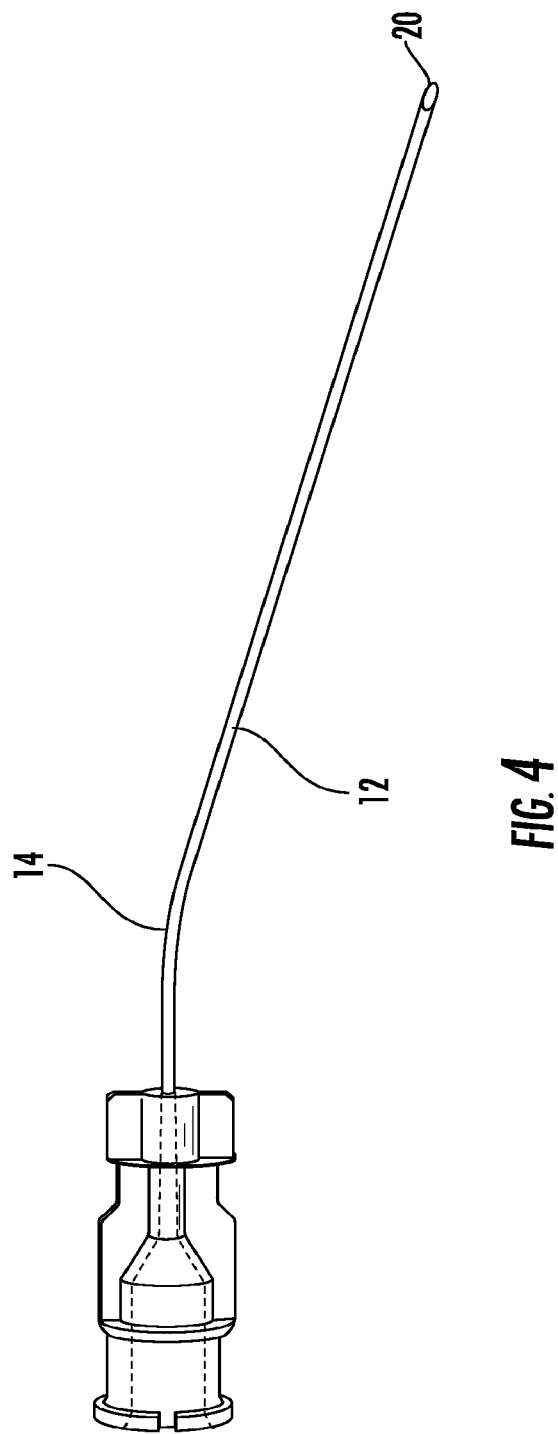
FIG. 4 is a side elevation view of an embodiment described herein.

As shown in FIG. 2, a plunger 16 is connected to an ejector 18. The ejector 18 can be an obturator, flexible metal wire, or other suitable structure. The plunger 16 can be connected to the ejector 18 by a number of means, including but not limited to gluing, welding, fusing, or any other manner suitable for connecting the ejector 18 to the plunger 16. The plunger 16 and ejector 18 can also be formed into a single integrated component during manufacturing. In an embodiment, medical grade adhesive is used to glue the ejector 18 to the plunger 16. The ejector 18 is longer than the needle 12 so that when the ejector 18 is inserted through the syringe 10 and into the hollow bore needle 12 and the plunger 16 is then fully plunged into the syringe 10, the ejector 18 will reach the tip 20 of the needle 12 (as shown in FIG. 9). In FIGS. 8 and 9, the needle 12 has been made transparent so that the ejector 18 (in FIGS. 8 and 9) and drug eluting implant 2 (in FIG. 8) can be seen inside of the needle 12.

Referring now to FIGS. 1, 7-9, and 12, the method and apparatus described herein can utilize or include an implant, such as a drug eluting implant 2. In an embodiment, the drug eluting implant 2 can be or can contain a bio absorbable material and/or slow release material that, once inserted into the nasal turbinate 4 or nasal polyp 6, allows one or more drugs to be released over a period of time. The drug eluting implant 2 can, over various periods of time depending on the drug and formulation, release the drug(s) into the local tissue. For example, if the drug eluting implant 2 is a steroid eluting implant that is implanted into the turbinate 4, the steroid will shrink the reactive tissue in the turbinate 4 and decrease the reactiveness of the tissue to allergens in a manner similar to nasal sprays. Similarly, if the drug eluting implant 2 is a steroid eluting implant that is implanted into a nasal polyp 6, the steroid will shrink the reactive tissue in the polyp 6 and decrease the reactiveness of the tissue to allergens, also in a manner similar to nasal sprays.

However, unlike nasal sprays, the drug eluting implant 2 is often implanted into the patient by another person, such as by a physician in a physician's office. In further contrast to nasal sprays, the drug eluting implant 2 can be left implanted in the patient for weeks or months, and the drugs of the drug eluting implant 2 can be slowly released over this extended period of time. The extended time period of drug release of the drug eluting implant 2 can obviate the need for a patient to use a nasal spray once per day or even multiple times per day.

In an embodiment, the drug eluting implant 2 is made of a bio absorbable material, such that the drug eluting implant 2 is eventually absorbed into the tissue of the patient (for example, once all of the drugs of the drug eluting implant 2 have been released). In an alternative embodiment, the drug eluting implant 2 can be removed after a period of time if desired.

The time period of drug release of the drug eluting implant 2 can be an extended period of time, and can be at least one day, at least one week, at least one month, or at least one year. In an embodiment, the drug eluting implant 2 can be or can include a slow release poly(lactic-co-glycolic acid) scaffold that can include one or more drugs that can be wrapped or printed onto it.

The drug eluting implant 2 can contain or can be composed of one or more types of drugs, including but not limited to steroids, corticosteroids, antihistamines, hormones, antibiotics, anticholinergic agents, and/or other types of drugs. As used herein, the term "drug" includes drugs, medicines, active ingredients, and the like. In an embodiment, the drug eluting implant 2 contains both a slow release steroid as well as a slow release antihistamine, thus making it both a steroid eluting implant as well as an antihistamine eluting implant.

The drug eluting implant 2 can be various sizes and shapes. In the embodiment shown in FIGS. 1, 7-9, and 12, the drug eluting implant 2 is in the shape of a rod and may resemble a piece of monofilament fishing line. In an embodiment the drug eluting implant can have a length of between about three inches and about six inches, and can have a diameter of between about 0.004 millimeters and about 2 millimeters. In an embodiment the drug eluting implant 2 can be flexible, while in another embodiment the drug eluting implant 2 can be rigid. The drug eluting implant can also be of a spherical shape, such as one or more small beads of drug eluting material, as is shown by drug eluting implant 40 in FIG. 12.

Referring to FIG. 1, the nasal turbinates include the superior turbinate 30, middle turbinate 32, and inferior turbinate 34. Although in FIG. 1 the drug eluting implant 2 is shown implanted in the inferior turbinate 34, the drug eluting implant 2 can also be implanted in the superior turbinate 30 or the middle turbinate.

In operation of an embodiment, a drug eluting implant 2 is implanted into a nasal turbinate 4. The syringe 10, needle 12, plunger 16, and ejector 18 can be used in concert to implant a drug eluting implant 2 into a nasal tissue. In FIG. 1, a drug eluting implant 2 is implanted into a nasal turbinate 4. More particularly, the drug eluting implant 2 of FIG. 1 is implanted into the submucosal plane of the inferior turbinate 34. In operation, this can be accomplished by connecting the plunger 16 to the ejector 18. The ejector 18 can then be passed through the syringe 10 and inserted into the hollow bore of the needle 12. If the drug eluting implant 2 is to be implanted at a later time, the plunger 16 can be fully depressed into the syringe 10, and the syringe 10, needle 12, plunger 16 and ejector 18 assembly can be stored until it is ready to be used.

Figure 5:
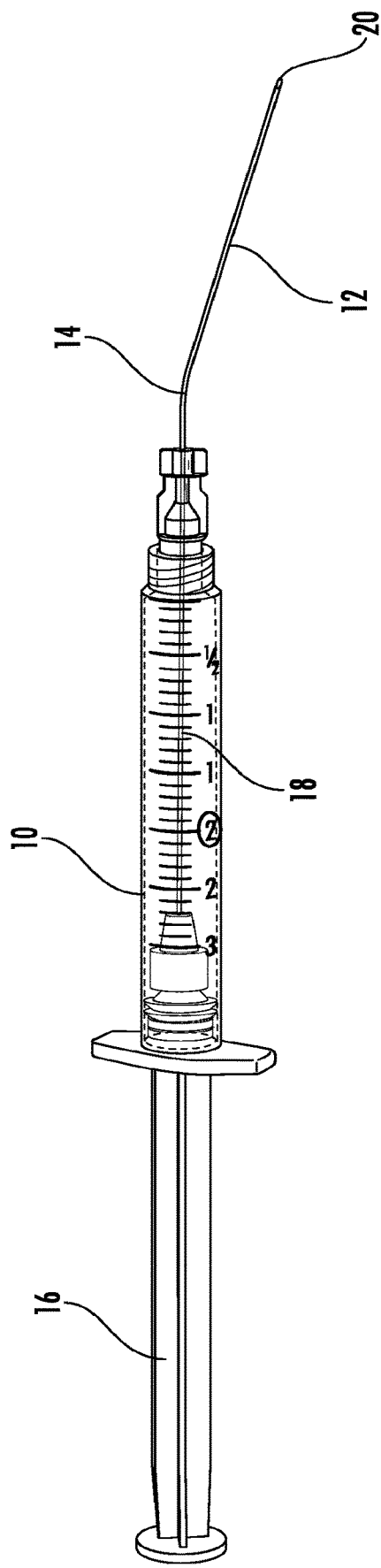
FIG. 5 is a side elevation view of an embodiment described herein.
Figure 6:
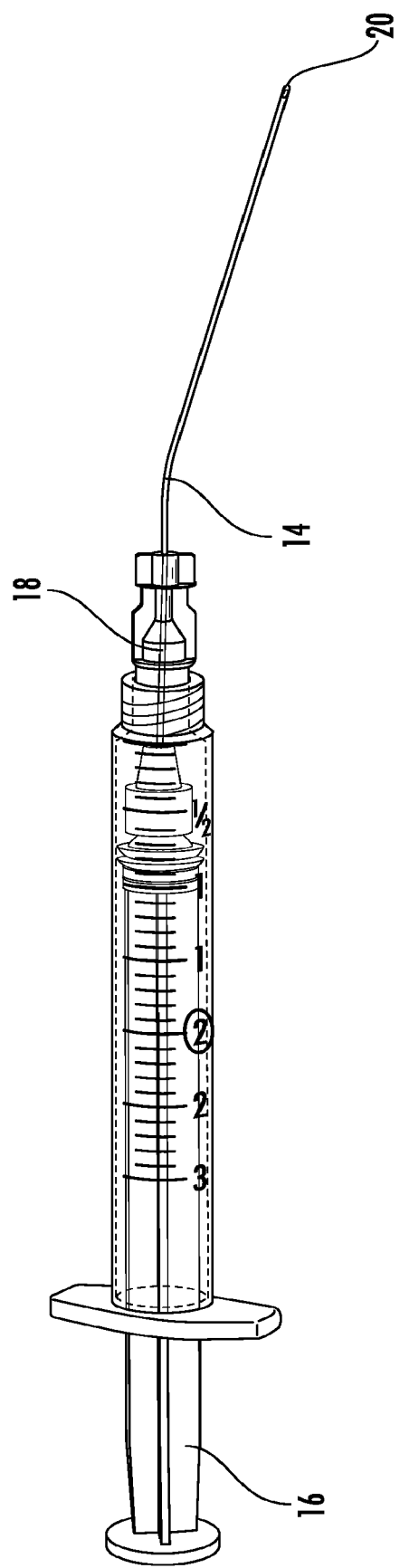
FIG. 6 is a side elevation view of an embodiment described herein.

When the syringe 10, needle 12, plunger 16 and ejector 18 assembly is ready to be used to implant a drug eluting implant 2 into the turbinate of a patient, the plunger 16 is first fully retracted as shown in FIG. 5. This partially backs the ejector 18 out of the hollow bore needle 12, thus creating a void within a portion of the hollow bore needle 12 beginning at the tip 20 of the hollow bore needle 12. The drug eluting implant 2 is then placed into this void in the needle 12 by inserting the drug eluting implant 2 into the tip 20 of the needle 12 until the drug eluting implant 2 is fully contained within the hollow bore of the needle 12 (as shown in FIG. 8).

Next, the tip 20 of the needle 12 is inserted at the anterior end of the turbinate 4, and then further inserted into the submucosal plane of the inferior turbinate. Once the needle 12 is properly positioned within the turbinate 4, the plunger 16 is depressed into the syringe 10, thus forcing the ejector 18 towards the tip 20 of the needle 12. As the plunger 16 is fully depressed, the drug eluting implant 2 is ejected (as shown in FIG. 9). As the plunger 16 is depressed, the needle 12 is simultaneously withdrawn from the turbinate 4. Depressing the plunger 16 until the plunger 16 is fully depressed while simultaneously withdrawing the needle 12 from the turbinate 4 ejects the drug eluting implant 2 from the needle 12 and implants the drug eluting implant 2 into the tract of the turbinate 4 that was formed by the insertion of the needle 12. The drug eluting implant 2 then remains in the turbinate 4 and slowly releases its drugs over a period of time. The method of implanting a drug eluting implant 2 into the turbinate 4 can be periodically repeated, such as once a month or once every three to four months when the drug eluting implant's supply of drugs is depleted. Doing so can create a relatively permanent form of treatment for a patient without the need for the daily use of a nasal spray.

Figure 12:
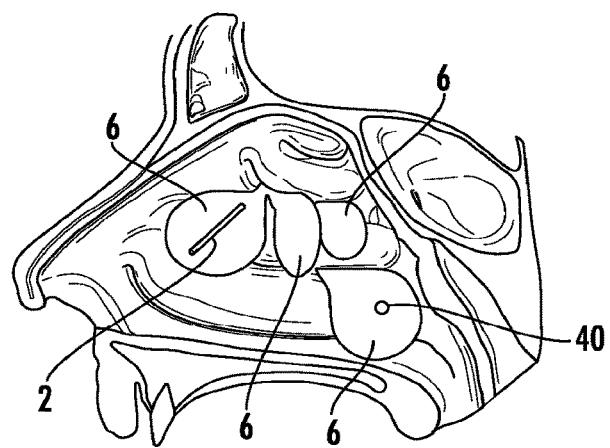
FIG. 12 is a cross sectional side view of the sinus region of a person and shows an embodiment described herein.

In operation of another embodiment, a drug eluting implant 2 is implanted into a nasal polyp 6. As shown in FIG. 12, drug eluting implants 2 and 40 are implanted into nasal polyps 6. In operation, this can be accomplished by connecting the plunger 16 to the ejector 18. The ejector 18 can then be passed through the syringe 10 and inserted into the hollow bore of the needle 12. If the drug eluting implant 2 is to be implanted at a later time, the plunger 16 can be fully depressed into the syringe 10, and the syringe 10, needle 12, plunger 16 and ejector 18 assembly can be stored until it is ready to be used.

When the syringe 10, needle 12, plunger 16 and ejector 18 assembly is ready to be used to implant a drug eluting implant 2 or 40 into the nasal polyp of a patient, the plunger 16 is first fully retracted as shown in FIG. 5. This partially backs the ejector 18 out of the hollow bore needle 12, thus creating a void within a portion of the hollow bore needle 12 beginning at the tip 20 of the hollow bore needle 12. The drug eluting implant 2 is then placed into this void in the needle 12 by inserting the drug eluting implant 2 into the tip 20 of the needle 12 until the drug eluting implant 2 is fully contained within the hollow bore of the needle 12 (as shown in FIG. 8).

Next, the tip 20 of the needle 12 is inserted into the nasal polyp 6. Once the needle 12 is properly positioned within the polyp 6, the plunger 16 is depressed into the syringe 10, thus forcing the ejector 18 towards the tip 20 of the needle 12. As the plunger 16 is fully depressed, the drug eluting implant 2 and/or 40 is ejected. As the plunger 16 is depressed, the needle 12 is simultaneously withdrawn from the polyp 6. Depressing the plunger 16 until the plunger 16 is fully depressed while simultaneously withdrawing the needle 12 from the polyp 6 ejects the drug eluting implant 2 and/or 40 from the needle 12 and implants the drug eluting implant 2 and/or 40 into the tract of the polyp 6 that was formed by the insertion of the needle 12. The drug eluting implant 2 and/or 40 then remains in the polyp 6 and slowly releases its drugs over a period of time. The method of implanting a drug eluting implant 2 and/or 40 into the polyp 6 can be periodically repeated, such as once a month or once every three to four months when the drug eluting implant's supply of drugs is depleted. Doing so can create a relatively permanent form of treatment for a patient without the need for the daily use of a nasal spray.

In still other embodiments, instead of using the syringe 10, needle 12, plunger 16 and ejector 18 assembly to implant the drug eluting implant into the turbinate 4 or polyp 6, the drug eluting implant can be implanted into the turbinate 4 or polyp 6 in a number of other ways. For example, the drug eluting implant can be a long and rigid spear like rod that is sharpened at one end. The rod can be sufficiently long so that it can be held at one end while inserting the opposite sharpened end into the turbinate or polyp. The rod can then be snapped or cut off, for example flush with the turbinate or polyp, such that a drug eluting portion of the rod remains implanted in the turbinate or polyp.

The foregoing description and accompanying drawings illustrate the principles, exemplary embodiments, and modes of operation of the invention. However, the invention should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the invention.

I claim:

1. A method for delivering a drug into nasal tissue comprising:
   a) placing a monolithic drug eluting implant into a needle of a syringe, wherein the implant is between about 3 inches and about 6 inches in length;
   b) inserting the needle at an anterior end of a nasal turbinate;
   c) inserting the needle into a submucosal plane of the turbinate;
   d) implanting the monolithic drug eluting implant into the submucosal plane of the turbinate; and
   e) withdrawing the needle from the turbinate,
   wherein the monolithic drug eluting implant is present in the nasal turbinate for at least one month.

2. The method of claim 1 wherein said placing the drug eluting implant into the needle of the syringe further comprises placing a slow release poly(lactic-co-glycolic acid) scaffold into the needle of the syringe.

3. The method of claim 1 wherein said implanting the drug eluting implant into the submucosal plane of the turbinate further comprises implanting a slow release poly(lactic-co-glycolic acid) scaffold into the submucosal plane of the turbinate.

4. The method of claim 1 wherein said implanting the drug eluting implant into the submucosal plane of the turbinate further comprises depressing a plunger of the syringe such that an ejector connected to the plunger ejects the drug eluting implant into the submucosal plane of the turbinate.

5. The method of claim 4 further comprising simultaneously performing said depressing a plunger of the syringe such that an ejector connected to the plunger ejects the drug eluting implant into the submucosal plane of the turbinate and said withdrawing the needle from the turbinate.

6. The method of claim 1 wherein said implanting the drug eluting implant into the submucosal plane of the turbinate further comprises implanting the drug eluting implant into an inferior turbinate.

7. The method of claim 1 wherein said implanting the drug eluting implant into the submucosal plane of the turbinate further comprises implanting a steroid eluting implant into the submucosal plane of the turbinate.

8. The method of claim 1 wherein said implanting the drug eluting implant into the submucosal plane of the turbinate further comprises implanting an antihistamine eluting implant into the submucosal plane of the turbinate.

9. The method of claim 8 wherein said implanting the drug eluting implant into the submucosal plane of the turbinate further comprises implanting a steroid eluting implant into the submucosal plane of the turbinate.

10. A method for delivering a drug into nasal tissue comprising:
   a) implanting a monolithic drug eluting implant into a nasal turbinate; and
   b) leaving the monolithic drug eluting implant in the nasal turbinate for at least one month,
   wherein the monolithic drug eluting implant is between about 3 inches and about 6 inches in length.

* * * * *